United States Patent
Kyrkanides et al.

(10) Patent No.: US 10,350,147 B2
(45) Date of Patent: Jul. 16, 2019

(54) ENAMEL PRODUCTS AND METHODS OF USE

(71) Applicant: The Research Foundation for The State University of New York, Albany, NY (US)

(72) Inventors: Stephanos Kyrkanides, Lexington, KY (US); Li Ma, Stonybrook, NY (US); Sabine Brouxhon, Lexington, KY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/305,263

(22) PCT Filed: Apr. 27, 2015

(86) PCT No.: PCT/US2015/027798
§ 371 (c)(1),
(2) Date: Oct. 19, 2016

(87) PCT Pub. No.: WO2015/168022
PCT Pub. Date: Nov. 5, 2015

(65) Prior Publication Data
US 2017/0035661 A1 Feb. 9, 2017

Related U.S. Application Data

(60) Provisional application No. 61/984,814, filed on Apr. 27, 2014.

(51) Int. Cl.
| | |
|---|---|
| *A61K 6/033* | (2006.01) |
| *A61C 5/77* | (2017.01) |
| *A61K 35/36* | (2015.01) |
| *A61K 35/32* | (2015.01) |
| *A61K 35/28* | (2015.01) |
| *A61C 5/70* | (2017.01) |
| *C12N 5/071* | (2010.01) |
| *G16H 20/40* | (2018.01) |
| *A61C 13/00* | (2006.01) |

(52) U.S. Cl.
CPC ............... *A61K 6/033* (2013.01); *A61C 5/70* (2017.02); *A61C 5/77* (2017.02); *A61K 35/28* (2013.01); *A61K 35/32* (2013.01); *A61K 35/36* (2013.01); *C12N 5/0629* (2013.01); *A61C 13/0004* (2013.01); *A61F 2310/00359* (2013.01); *C12N 2501/10* (2013.01); *C12N 2501/105* (2013.01); *C12N 2501/11* (2013.01); *C12N 2501/15* (2013.01); *C12N 2501/825* (2013.01); *C12N 2501/91* (2013.01); *C12N 2501/998* (2013.01); *C12N 2513/00* (2013.01); *C12N 2533/18* (2013.01); *C12N 2533/90* (2013.01); *G16H 20/40* (2018.01)

(58) Field of Classification Search
CPC ........ A61K 6/033; A61K 35/36; A61K 35/28; A61K 35/32; C12N 2501/11; C12N 2501/105; C12N 5/0629; C12N 2533/90; C12N 2533/18; C12N 2513/00; C12N 2501/15; C12N 2501/825; C12N 2501/998; C12N 2501/91; C12N 2501/10; A61C 13/0004; A61C 5/70; A61C 5/77; G16H 20/40; A61F 2310/00359
See application file for complete search history.

(56) References Cited

U.S. PATENT DOCUMENTS

| | | |
|---|---|---|
| 2009/0286760 A1 | 11/2009 | Chen |
| 2011/0027235 A1 | 2/2011 | Gregory et al. |
| 2012/0148538 A1 | 6/2012 | Park et al. |
| 2012/0214217 A1 | 8/2012 | Grogan et al. |
| 2014/0093481 A1 | 4/2014 | Mao et al. |

OTHER PUBLICATIONS

Elaut et al. Molecular mechanisms underlying the dedifferentiation process of isolated hepatocytes and their cultures. Curr Drug Metab. Aug. 2006;7(6):629-60. Abstract only (Year: 2006).*
Talchai et al. Pancreatic B-Cell Dedifferentiation as Mechanism of Diabetic B-Cell Failure. Cell. Sep. 14, 2012; 150(6): 1223-1234. (Year: 2012).*
Dimitrova-Nakov et al. Deletion of Serotonin 2B Receptor Provokes Structural Alterations of Mouse Dental Tissues. Calcif Tissue Int (2014) 94:293-300. (Year: 2014).*
Moiseiwitsch et al. Stimulation of Murine Tooth Development in Organotypic Culture by the Neurotransmitter Serotonin. Archs oral BioL vol. 41, No. 2, pp. 161-165, 1996 (Year: 1996).*
Zhang et al. Transforming Growth Factor b1 Signal is Crucial for Dedifferentiation of Cancer Cells to Cancer Stem Cells in Osteosarcoma. Stem Cells 2013;31:433-446. (Year: 2013).*
Casey et al. Mammary Epithelial Cells Treated Concurrently with TGF-a and TGF-b Exhibit Enhanced Proliferation and Death. Exp Biol Med 232:1027-1040, 2007 (Year: 2007).*

(Continued)

*Primary Examiner* — Taeyoon Kim
(74) *Attorney, Agent, or Firm* — Fox Rothschild LLP

(57) ABSTRACT

Described herein are three-dimensional (3D) culture systems that can be used to produce enamel organoids that generate enamel products. The invention features methods of culturing a variety of cell types to produce such enamel organoids; the organoids themselves; enamel products generated by the organoids; and methods of fashioning the enamel products into surgical restorations, including dental restorations and other prostheses.

8 Claims, 6 Drawing Sheets

(56) References Cited

OTHER PUBLICATIONS

Zangrossi et al. Oct-4 Expression in Adult Human Differentiated Cells Challenges Its Role as a Pure Stem Cell Marker. Stem Cells 2007;25:1675-1680 (Year: 2007).*
Arakaki et al. Role of Epithelial-Stem Cell Interactions during Dental Cell Differentiation. The Journal of Biological Chemistry vol. 287, No. 13, pp. 10590-10601, Mar. 23, 2012 (Year: 2012).*
Youn et al. Cell Phenotype in Normal Epithelial Cell Lines with High Endogenous N-Cadherin: Comparison of RPE to an MDCK Subclone. (Invest Ophthalmol Vis Sci. 2006;47:2675-2685 (Year: 2006).*
Tadeu et al. Epithelial Stem Cells in Adult Skin. Curr Top Dev Biol. 2014 ; 107: 109-131. (Year: 2014).*
Harada et al. Epithelial stem cells in teeth. Odontology (2002) 90:1-6 (Year: 2002).*
Turabelidze et al. Intrinsic Differences between Oral and Skin Keratinocytes. PLoS ONE 9(9): e101480. p. 1-10 (Year: 2014).*
Shah et al. Neutralisation of TGF-b1 and TGF-b2 or exogenous addition of TGF-b3 to cutaneous rat wounds reduces scarring. Journal of Cell Science 108, 985-1002 (1995) (Year: 1995).*
Honda and Hata, "Enamel Tissue Engineering," *Tissue Engineering*, Daniel Eberli (Ed.), ISBN: 978-953-307-079-7, InTech, Available from www.intechopen.com/books/tissue-engineering/enamel-tissue-engineering, 2010.
Huang et al., "Bioactive nanofibers instruct cells to proliferate and differentiate during enamel regeneration", *J. Bone & Mineral Res.*, 23(12):1995-2006, 2008.
Riksen et al., "Serotonin and fluoxetine receptors are expressed in enamel organs and LS8 cells and modulate gene expression in LS8 cells: Effect of serotonin and SSRI on LS8 cells", *Eur. J. Oral Sciences*, 118(6):566-573, 2010.
Heymann et al., "E- and N-Cadherin Distribution in Developing and Functional Human Teeth under Normal and Pathological Conditions," American Journal of Pathology,160(6):2123-2133, 2002.
Moiseiwitsch et al., "Regulation by Serotonin of Tooth-Germ Morphogenesis and Gene Expression in Mouse Mandibular Explant Cultures," Archives of Oral Biology, 43:789-800, 1998.

* cited by examiner (a)

(b)

(c)

ENAMEL PRODUCTS AND METHODS OF USE

CROSS REFERENCE TO RELATED APPLICATIONS

This application is a U.S. National Stage application, filed under 35 USC § 371, of International Application No. PCT/US2015/027798, filed Apr. 27, 2015, which claims the benefit of the filing date of U.S. Provisional Application No. 61/984,814, which was filed Apr. 27, 2014, the contents of which are hereby incorporated by reference in their entirety.

FIELD OF THE INVENTION

The present invention relates to enamel products that can be used to fashion restorative dental products and skeletal prostheses, including prostheses useful in repairing dentofacial defects (e.g., cleft palate). The enamel products are also useful in replacing portions of other bones that have been damaged by trauma or disease and in cosmetic surgeries. Compositions and methods for producing, fashioning, and implanting a dental restoration or skeletal prosthesis from the enamel products, including methods by which the enamel products are shaped with the assistance of CAD/CAM technology or assembled with a 3D printer, are also within the scope of the invention.

BACKGROUND

Enamel is one of the major tissues within teeth. It is formed during early development, before the tooth breaks through the gum, and it covers the visible portion of the tooth. During development, epithelial cells within the enamel organ differentiate into ameloblasts, which produce the hardened, high mineral-content enamel. More specifically, the enamel organ appears naturally in vivo as an aggregate of cells in histologic sections of the developing tooth, and it includes the inner enamel epithelium, where ameloblasts reside, the outer enamel epithelium, the stratum intermedium, and the stellate reticulum. The dental organ is comprised of the enamel organ and mesenchyme.

Maintaining and repairing enamel are primary concerns for dentists and others working in the field of dentistry. This is challenging because enamel demineralizes in the mouth and does not regenerate. Although mechanisms for remineralizing teeth are known, the state of equilibrium can easily be tipped toward demineralization. For example, bacteria within the dental plaque (e.g., *Streptococcus mutans*) can produce organic acids that, particularly in the presence of sugars, reduce the pH in the mouth, promoting demineralization and dental caries. Engineering enamel is obviously desirable, but this has proven difficult due to not only a lack of ameloblasts in erupted teeth, but also a developmental requirement; thus far, the epithelial cells that can differentiate into ameloblasts must interact with mesenchymal cells to develop properly. Previous efforts to produce enamel have included both cell-based and cell-free strategies. Commonly, cell-based strategies rely on the development of a stable cell line that is combined with mesenchymal cells in Matrigel™ (a gelatinous and protein-containing cell culture substrate) and transplanted into an animal where enamel is generated in vivo (see, e.g., DenBesten et al., *Connect Tissue Res.* 38(1-4):3-8, 1998; DenBesten et al., *Eur. J. Oral Sci.,* 107(4):276-81, 1999; Nakata et al., *Biochem. Biophys. Res. Commun.,* 308(4):834-839, 2003; Honda et al., *Cells Tissues Organs* 189(1-4):261-267, 2009; Shinmura et al., *J. Cell. Physiol.* 217(3):728-738, 2008; Nakagawa et al., *J. Dental Res.* 88(3):219-223, 2009; Takahashi et al., *In Vitro Cell Dev. Biol. Anim.,* 46(5):457-468, 2010; Liu et al., *J. Tissue Eng. Regen. Med.* 7:934-943, 2012; Hu et al., *J. Dent. Res.,* 85(5):416-421, 2006; and Chen, *Arch. Oral Biol.* 37: 771-778, 1992). As enamel contains about 97% hydroxyapatite and has no cells, synthetic processes are also possible (see, e.g., Yamagishi et al., Nature 433:819, 2005; and Brunton et al., *Br. Dental J.* 215:741, 2013). Enamel products made by cell-free protocols have been tested in clinical trials and were shown to be effective in treating early, minor caries (Yamagishi et al., *Nature* 433:819, 2005; and Brunton et al., *Br. Dental J.* 215:741, 2013).

SUMMARY

The present invention is based, in part, on our development of culture systems, including in vitro, 3-dimensional (3D), cell-based culture systems, that provide an environment for the growth of enamel organoids that contain ameloblast-like cells that generate enamel products. In that sense, the culture systems of the invention replicate the enamel organ. Unlike methods used to date, the culture systems described herein can produce an enamel product without employing a naturally occurring enamel organ or relying on dental mesenchyme or mesenchymal cells.

The present methods can be carried out using a variety of different cell types, which are placed into a cell culture system that is configured to allow for 3D growth of the cultured cells into enamel organoids. Where the cells placed into culture do not produce amelogenin (e.g., where the cells initially cultured are differentiated cells distinct from ameloblasts), the methods include steps whereby the cells are de-differentiated and then re-differentiated into ameloblast-like cells. Where the cells placed into culture are stem cells or precursor cells, the de-differentiation step can be omitted, and where the cells placed into culture are cells that produce amelogenin (e.g., primary cells) or cells of a cell line derived therefrom, both the de-differentiation step and the induction of amelogenin production can be omitted.

Accordingly, in a first aspect, the invention features methods of generating an enamel product in vitro by: (a) providing a differentiated cell in cell culture; (b) exposing the differentiated cell to an agent that induces dedifferentiation, thereby producing a dedifferentiated cell; (c) exposing the dedifferentiated cell to a serotonin receptor agonist, thereby producing an ameloblast-like cell that expresses amelogenin (e.g., by producing an extracellular matrix comprising amelogenin); and (d) exposing the extracellular matrix to a composition that induces mineralization, thereby producing an enamel product. In a second aspect, the invention features methods of generating an enamel product in vitro by: (a) providing a stem cell or precursor cell in cell culture; (b) exposing the stem cell or precursor cell to a serotonin receptor agonist, thereby producing an ameloblast-like cell that produces an extracellular matrix; and (c) exposing the extracellular matrix to a composition that induces mineralization, thereby producing an enamel product. In a third aspect, the invention features methods of generating an enamel product in vitro by: (a) providing a cell (e.g., an isolated ameloblast, an immortalized ameloblast, or a cell engineered to express amelogenin); and (b) placing the ameloblast in a culture system (e.g., a two- or three-dimensional culture system). One can maintain the culture to allow for cellular growth and division, and one can increase the density of the organoids in culture (e.g., by harvesting and re-plating or re-culturing them) to facilitate the formation of larger organoids that will more readily aggregate to form conglomerates. To facilitate cellular proliferation and/or increase the size of the enamel organoids that develop in culture, one can expose the cells to a composition (e.g., a cell culture medium) containing serum and/or a growth factor or combination of growth factors as described further below. Once the cells proliferate and produce an extracellular matrix comprising amelogenin, they are useful as an enamel product, and we may specify such products as unmineralized enamel products. These unmineralized enamel products can be used to fashion restorations and prostheses by, for example, three-dimensional printing. One can expose the unmineralized enamel products to an agent that induces mineralization, thereby generating a mineralized enamel product, which is also useful in fashioning restorations and prostheses (e.g., by 3D printing). The mineralized enamel products can be developed further by exposure to a reagent that reduces the amount of organic material in the enamel organoids. Thus, any of the methods can further include a step of removing organic material from the enamel organoids once they have reached a desired size. Enamel organoids that are mineralized and lack organic materials (e.g., that are free or substantially free or organic materials) may be especially amenable to CAD/CAM technology in order to produce restorations and prostheses.

In any embodiment where a differentiated cell is employed, the cell can be an epithelial cell (e.g., an oral epithelial keratinocyte), but the invention is not so limited; any differentiated cell that can be de-differentiated in cell culture and/or reprogrammed to begin expressing amelogenin (e.g., in an extracellular matrix) can be employed. In any embodiment, a cell in cell culture (e.g., a 3D culture) can be a primary cell. That is, whether the method of generating an enamel product involves culturing a differentiated cell, a stem or precursor cell, or an ameloblast, the cell can be one that is harvested from an animal and placed in cell culture. In other embodiments, the cell (whether a differentiated cell, stem cell, precursor cell, or ameloblast) may have been harvested from an animal and subsequently immortalized. Thus, the present methods can be carried out with primary cells or cells of a cell line. Moreover, the cell can be obtained from a variety of sources, including a mammal, such as a human. Any of the cells employed can be genetically modified (e.g., by recombinant techniques to alter the gene products expressed by the cells).

Where employed, the agent that induces dedifferentiation can be a transforming growth factor (e.g., TGFβ (e.g., TGFβ1)). The dedifferentiated cell can be one that expresses a marker normally associated with a stem cell (e.g., N-cadherin or octamer-binding transcription factor 4 (Oct-4)) but not a marker normally associated with a mature phenotype (e.g., dedifferentiated epithelial cells may fail to express the epithelial marker E-cadherin).

Where employed, the serotonin receptor agonist can be serotonin, an azapirone, a triptan, LY-334,370, lasmiditan, lysergic acid diethylamide, mescaline, 2,5-dimethoxy-4-bromophenethylamine, lorcaserin, cisapride, tegaserod, prucalopride, or AS-19; a salt, hydrate, or analog thereof (e.g., N,N-dimethyltryptamine); or any combination thereof.

The composition that induces mineralization can include calcium and/or phosphate (e.g., a mineral containing calcium or phosphate).

To variously support cell growth and differentiation, the cell cultures can include one or more growth factors of the epidermal growth factor (EGF) family, the insulin-like growth factor (IGF) family, the fibroblast growth factor (FGF) family, or others (e.g., a platelet-derived growth factor; PDGF; see also, below).

Any of the cell cultures can include (e.g., within the culture substrate or medium) laminin, collagen IV, a heparan sulfate proteoglycan, entactin/nidogen, or a solubilized basement membrane preparation extracted from the Engelbreth-Holm-Swarm (EHS) mouse sarcoma. In any embodiment, the cell culture can be configured to permit cells (e.g., an ameloblast or ameloblast-like cell) to proliferate into a 3-dimensional cluster of cells, which we may refer to as an enamel organoid. An ameloblast or ameloblast-like cell can be exposed in the present culture systems to a composition that includes serum and/or one or more growth factors (e.g., an EGF, IGF, FGF, TGF, or nerve growth factor).

In any of the present methods, the enamel organoids can be treated to reduce or remove the organic material therein. For example, the enamel organoids can be treated with (e.g., immersed in) sodium hypochloride and/or a soap/detergent (e.g., Triton-X100). If desired, the treatment can include immersing the enamel organoids in an ultrasonic bath and/or exposing them to heat (e.g., dry heat) to facilitate the destruction and/or removal of the organic material. The enamel products as described herein can therefore be free or substantially free of organic matter.

In another aspect, the invention features an enamel product made by a method described herein. The product can be harvested and packaged for sale (together with instructions for use) or can be fashioned into a surgical restoration, which can then also be packaged for sale. To arrive at a restoration of the present invention, one could provide an enamel product as described herein and subject the product to a process by which it is further assembled or shaped. For example, the enamel product can be subjected to impression molding or shaping as indicated by a computer aided design package. In one embodiment, the enamel product can be shaped to include an indentation and/or protrusion, and the indentation on a first enamel product can be formed to engage a protrusion on a second enamel product. As a result, one can assemble larger products from a plurality of smaller products, and these larger products can then be further shaped into restorations suitable for repairing larger defects (e.g., a defect in a long bone such as the femur, a flat bone such as the scapula, or an irregular bone such as a bone in the pelvis or spine).

In one embodiment, the surgical restoration is a dental restoration (e.g., a crown, a veneer, a corresponding scaffold, an inlay, an onlay, a full denture, a partial denture, a bridge, or the like). In another embodiment, the surgical restoration is an orthopedic prosthesis.

In another aspect, the invention features cell culture systems including cells that produce amelogenin. The systems can be configured as 3-dimensional systems that allow the cells to form enamel organoids. The cells that produce amelogenin may be cells that do so naturally (e.g., primary ameloblasts or immortalized primary cells) or cells that have been manipulated to express amelogenin by, for example, exposure to a serotonin receptor agonist or by genetic engineering. In various embodiments, the methods described herein can be carried out in 3D cultures that include scaffolds comprising a biological polymer (e.g., collagen, silk protein, alginate, chitosan, peptides, hyaluronic acid, derivatives thereof that retain the ability to support cell growth in three dimensions, or any mixture or combination thereof). In other embodiments, the scaffold can include a ceramic. Three-dimensional culture systems are known in the art. One can consult, for example, Sumita et al. (*Biomaterials* 27:3238-3248, 2006) and Zhang et al. (*Japanese Dental Science Rev.* 49:14-26, 2013).

Based on our studies to date, we have identified similarities between the enamel organs that naturally develop in vivo and the enamel organoids in our in vitro 3D culture systems. For example, in both cases, spheroid cellular clusters form that contain polarized columnar peripheral borderline cells that express amelogenin. In addition to amelogenin (or alternatively), other enamel markers including ameloblastin, enamelin, and tuftelin may be present. An extracellular, mineralizable matrix containing amelogenin is also formed, providing structural and chemical support for cells, including the borderline cells just mentioned; this extracellular matrix serves as the matrix for mineralization of the enamel product. Amelogenin protein is highly expressed by enamel cells, and this protein undergoes self-assembly to form nanospheres that interact with hydroxyapatite crystals and orient crystal growth in a direction perpendicular to the surface. The enamel products of the invention can be crystallized, and in various embodiments their crystal structure will differ from that of naturally occurring tooth enamel.

The spherical enamel organ that develops in vivo and the enamel organoid within the present cultures both grow by expanding in three dimensions. As the peripheral borderline cells proliferate, they lay down an extracellular matrix that comprises the basis for mineralization and enamel or an enamel product. Because the physical properties of the enamel produced in our culture systems are expected to be similar to those found in the natural tooth, we expect our enamel product will effectively minimize microleakage when fitted on prepared teeth and, therefore, reduce the risk of dental caries. In addition, restorations fashioned using the material of the invention may provide a more natural appearance and be more readily accepted by dentists and their patients. The rising costs of metal and porcelain materials also make the fabrication of enamel products that are produced as described herein cost effective.

Although the products employed for enamel restorations are currently made from materials that have different physical properties from the naturally occurring enamel, they have sufficiently similar properties to allow them to be used in a wide variety of surgical restorations. It is our current expectation that the physical properties of the present enamel products will be similar to those of naturally occurring enamel, lending distinct advantages to restorations produced using an enamel product as described herein. The hardness of the enamel product incorporated in a surgical restoration can be varied by altering the degree of mineralization. A restoration prepared for the surface of a tooth would likely require the highest mineral content while prostheses for bone replacement or augmentation can be mineralized to a lesser degree. Where the restoration is applied to replace cartilage or to reshape a cartilaginous feature (e.g., the nose or ears), the mineral content can be even lower. Thus, in various embodiments, the hardness of the enamel product can be substantially the same as that of tooth enamel, bone, or cartilage.

By "about" we mean plus-or-minus 10%. For example, about 10 µg is 9-11 µg, inclusive.

By "ameloblast-like cell" we mean a biological cell that lays down an extracellular matrix (ECM) containing amelogenin that serves as a scaffold for mineralization in a culture system as described herein.

By "differentiated cell" we mean a cell that is recognizable as a specialized cell type other than an ameloblast. For example, the differentiated cell can be an epithelial cell (e.g., an oral epithelial keratinocyte), a liver cell, a muscle cell, or a neuron. A differentiated cell, as defined herein, does not produce natural enamel but can be reprogrammed in cell culture to produce an enamel product. A "dedifferentiated cell" is one that was previously recognizable as a specialized cell type but no longer has at least one of the formerly recognized traits (e.g., one of the traits identifying it as a differentiated cell). For example, a dedifferentiated oral keratinocyte may no longer express an epithelial marker such as E-cadherin, keratin, a desmosomal protein (e.g., a desmoglein or desmocollin), or a cornified envelope protein; a dedifferentiated liver cell may no longer express a major plasma protein (e.g., serum albumin or C-reactive protein), a carrier protein (e.g., albumin, ceruloplasmin, transcortin, haptoglobin, hemopexin, IGF binding protein, retinol binding protein, transthyretin, or transferrin), a hormone (e.g., IGF-1, thrombopoietin, or hepcidin); or an apolipoprotein; a dedifferentiated muscle cell may no longer express actin or myosin; and a dedifferentiated neuron may no longer express neurotransmitters. Dedifferentiated cells useful in the present methods include cells that express a serotonin receptor and which are capable of expressing amelogenin following exposure to a serotonin receptor agonist. Dedifferentiated cells may also, but do not necessarily, express the mesenchymal marker N-cadherin or the stem cell marker OCT4.

An "enamel organ" refers to an aggregate of cells naturally occurring in vivo, while an "enamel organoid" refers to a cellular construct developed in vitro (in cell culture, including cell cultures configured for cells to expand in three dimensions) as described herein.

By "extracellular matrix" we mean the collection of molecules secreted by a cell that provide structural and/or biochemical support to the cell and cells surrounding it. The ECM may include, but does not necessarily include, one or more of collagen (e.g., collagen IV), chondroitin sulfate, elastin, fibronectin, hyaluronic acid, keratin sulfate, laminin, proteoglycans (e.g., heparan sulfate proteoglycans), and entactin/nidogen.

Unless the context indicates otherwise, we use the term "in vitro" to refer to a cell culture.

A "primary cell" is a cell taken from a living organism and one that has not been immortalized as a cell line.

By "stem cell" or "precursor cell" we mean a pluripotent or multipotent cell that does not produce natural enamel or an enamel product but differentiates into a cell that can produce natural enamel or an enamel product when cultured according to the methods described herein; stem cells and precursor cells are less than fully differentiated. Generally, pluripotent stem cells undergo further specialization into multipotent progenitor cells that then give rise to functional cells. Stem cells and precursor cells useful in the present methods express serotonin receptors.

By "surgical restoration" we mean a composition implanted in or otherwise applied to a patient's body (e.g., through a surgical procedure) in order to improve a physical defect (e.g., a defect in a tooth or bone caused by disease or trauma) or to enhance a physical structure (e.g., in cosmetic surgery). For example, the defect can include a fissure, cavity, or crevice created by a degenerative disease, cancer, or an injury. The surgical restoration can be a dental restoration (i.e., a composition applied in a dental procedure that is or that includes an enamel product) or a skeletal prosthesis (i.e., a composition applied in a surgical procedure to repair (fully or partially) a dentofacial structure or a portion of a long, flat, or irregular bone). The surgical restorations can be fashioned from an enamel product using CAD/CAM technology. A "restorative dental product" or "dental restoration" can be a composition that is useful in restoring (fully or partially) the structure or appearance of a tooth. These compositions include crowns, veneers, corresponding scaffolds, inlays, onlays, a partial denture, full dentures, and bridges (e.g., fixed bridges). A dental restoration is a type of surgical restoration, and we may also use the term "surgical restoration" to refer to a method by which a composition as described herein, comprising or consisting of an enamel product, is administered to a patient. Any of the treatment methods described herein can include a step of identifying a patient (e.g., a human patient, whether a man, woman, or child) in need of treatment. Thus, the methods can include a step of identifying a patient having a dental, facial, or dentofacial defect (e.g., cleft palate); a patient having the disorder amelogenesis imperfecta; or a patient having a skeletal element (e.g., a bone in the face) in need of repair. The need may only be one perceived by the patient, as would likely be the case for cosmetic surgeries.

DETAILED DESCRIPTION

Figure 1A:
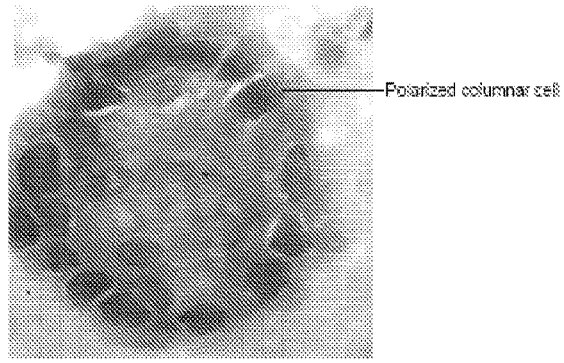
FIGS. 1(a)-1(c) are photomicrographs of 3D enamel organoids of the invention stained with hematoxylin and eosin (a), an anti-amelogenin antibody (b), and alizarin red (c), which stains calcium and indicates a mineralized organoid or enamel product.

In the paragraphs that follow, we describe compositions and methods for producing enamel organoids in vitro and for making and using surgical restorations from the enamel products produced by those organoids. The descriptions provided herein serve to illustrate, but do not limit, the invention.

The compositions and methods described herein can either be free of naturally occurring enamel organs, dental mesenchyme, and mesenchymal cells or can include or be carried out by using these moieties in combination with the cell types (e.g., stem cells, precursor cells, and differentiated cells (e.g., primary and immortalized cells)) and reagents (e.g., serotonin receptor agonists, growth factors, and mineralizing substances) described below.

Cells and cell types: Any cell or cell type that will produce an enamel product (whether unmineralized or mineralized or whether being substantially free of organic material (e.g., proteins, nucleic acids, and other cellular material)) under a condition described herein can be employed. These cells can be differentiated cells, which are induced to de-differentiate in culture, or they can be stem cells or precursor cells. In either event, the cells can originate from many different sources, including any number of eukaryotic tissues (e.g., blood, bone marrow, skin, or mucosal tissue). For example, a differentiated cell, a stem cell, or a precursor cell can be obtained from a vertebrate animal, such as a mammal (e.g., a human or other primate, a dog, cat, horse, cow, sheep, pig, goat, or rodent). A stem cell or a precursor/progenitor cell can be, for example, a hematopoietic stem cell, mesenchymal stem cell, epithelial stem cell from an adult organism, epithelial stem cell, adipose-derived stem cell, or dental pulp stem cell. The differentiated cell can be an epithelial cell (e.g., an epithelial keratinocyte, such as an oral epithelial keratinocyte, or an epithelial cell of the skin). Oral epithelial cells can be harvested from any area of the oral cavity in which they reside (e.g., the palate). In any embodiment, the cell can be immortalized and/or genetically modified.

More specifically, the enamel organoids can include or be generated from enamel organ epithelial (EOE) cells (e.g., the mouse EOE cells used by Chen et al. (1992) see also DenBesten et al., Connect Tissue Res. 38(1-4):3-8, 1998). As noted, the cells can be immortalized, and they can in that instance be, for example, the immortalized EOE cell line generated by DenBesten et al., PABSo-E (DenBesten et al., Eur. J. Oral Sci., 107(4):276-81, 1999). These cells have been passaged more than 55 times and maintained the characteristics of ameloblasts such as positive expression of amelogenin, MMP-20, and EMSP1 mRNA (markers for ameloblasts). The cells can also be spontaneously immortalized (e.g., the spontaneously immortalized mouse ameloblast cell line reported by Nakata et al. (Biochem. Biophys. Res. Commun., 308(4):834-839, 2003). Another useful cell type is the epithelial cell rests of Malassez (ERM cells; see Shinmura et al., J. Cellular Physiol. 217:728-738, 2008). ERM cells can be obtained from periodontal ligament tissue by explant culture, sub-cultured with non-serum medium, and expanded on 3T3-J2 feeder cell layers. The enamel organoids can also include or be generated from skin epithelial cells (see Liu et al., J. Tissue Eng. Regen. Med. 7:934-943, 2012). The enamel organoids can also include or be generated from bone marrow-derived cells. Hu et al. demonstrated reprogramming of these cells when they were cultured with dental mesenchyme (J. Dent. Res., 85(5):416-421, 2006).

Genetically modified cells: Either before or after they have been cultured and are producing an extracellular matrix to support mineralization, cells within the present constructs can be genetically modified to include a heterologous gene or gene construct. Methods for genetically engineering cells are well known in the art and include, for example, the electroporation methods utilized by Chen with mouse enamel organ epithelium (EOE) cells (Chen, Arch. Oral Biol. 37:771-778, 1992). If desired, the cells can be engineered to express one or more of the proteins expressed by an osteoblast or osteocyte. A cell can also be genetically modified to produce amelogenin or another marker of an ameloblast or to produce or produce more of a component of the ECM (including one or more of the components listed in the definition of the ECM). Thus, there are three means for producing useful cells in the methods of the invention: by providing a cell that naturally expresses an ECM and amelogenin (e.g., by isolating an ameloblast or a cell of an immortalized ameloblast cell line); by genetically engineering a cell to produce an ECM and amelogenin; or by re-programming a cell in culture (e.g., a differentiated cell, a stem cell, or other precursor) to express an ECM and amelogenin (e.g., by exposure to culture medium including serum and/or a growth factor or factors as described herein).

Substrates and culture conditions: For the culture systems described herein, the cells may be placed in a conventional two-dimensional culture initially, where they grow primarily in monolayers, and then transferred to a 3D culture, or they may be placed directly into the 3D culture. For example, where the methods employ differentiated cells that are modified through genetic or recombinant methods or by de- and re-differentiation to produce amelogenin, the cells can be placed initially into a two-dimensional culture that is not designed to support growth in three dimensions. When 3D growth is desired, a cell or cell type as described herein can be mixed with a substrate such as a basement membrane matrix (e.g., BD Matrigel™ from BD Bioscience, San Jose Calif.; catalog # 356234; see Hughes et al., *Proteomics* 10(9):1886-1890, 2010), and grown in vitro using growth media (e.g., DMEM-high sucrose). The BD Matrigel™ Basement Membrane Matrix is a soluble preparation extracted from the Engelbreth-Holm-Swarm (EHS) mouse sarcoma, comprised of extracellular matrix proteins including laminin, collagen IV, heparan sulfate proteoglycans, and entactin/nidogen. It also contains TGFβ, EGF, insulin-like growth factor, fibroblast growth factor, tissue plasminogen activator, and other growth factors that occur naturally in the EHS tumor. While the precise composition of the matrix can vary, it can include a mixture of extracellular matrix proteins and growth factors, and it can be derived from tumor cells (e.g., Engelbreth-Holm-Swarm (EHS) mouse sarcoma cells). The matrix can be one that, in the absence of other factors (e.g., a transdifferentiation factor as described herein), maintains a pluripotent cell in its pluripotent state (i.e., it promotes self-renewal). The cells (e.g., primary or immortalized oral keratinocytes) can also be initially placed into cultures supported by other media (e.g., CnT-02 growth medium (CELLNTEC).

In three-dimensional cultures, the cells can become multilayered or clustered with the layered and/or clustered cell growth being guided by scaffolds. For example, 3D cultures can be grown in AggreWell™ 400 plates (Stemcel Technologies, Grenoble, France). Each plate has six wells, and each well contains approximately 4,700 microwells measuring 400 μm in diameter. Enamel organoids can be transferred from such wells to ProtoTissue™ bioreactors (MC2 Biotek, Horsholm, Denmark) and incubated at 37° C. in 5% $CO_2$, 95% air in a humidified incubator, with the medium being exchanged every 2-5 days. Such bioreactors can support spheroid growth and the development of an extracellular matrix. More generally, one can use 3D cultures based on or generated by extracellular matrices or scaffolds (e.g., employing hydrogels), modified surfaces, rotating bioreactors, microcarriers, magnetic levitation, hanging drop plates, and/or magnetic 3D bioprinting. In scaffold-free techniques, one can employ low adhesion plates and micropatterned surfaces.

The cells can be maintained in culture until they reach a certain level of confluence. For example, the cells can be maintained until they are about 10-90% (e.g., about 30-40%, 40-50%, 50-60%, 60-70%, 70-80%, or 80-90%) confluent.

Treatments with a de-differentiation factor and a re-differentiation factor: The process disclosed herein can include: (1) dedifferentiation of a differentiated cell (e.g., an oral epithelial keratinocyte) by exposure to TGFβ1 (loss of E-cadherin; acquisition of N-cadherin+Oct4); (2) redifferentiation of the aforementioned dedifferentiated (e.g., stem cell-like) cells to enameloblast-like cells by exposure to serotonin (acquisition of amelogenin); (3) development of the 3D enamel organoid; and (4) mineralization of the enamel organoid, including its extracellular matrix (as evidenced by positive alizarin red staining). Epithelial cells typically form sheets, tubes, or vesicles in which they establish intimate associations with each other through specialized contact structures, including adherens junctions mediated by E-cadherin. Epithelial-to-mesenchymal transition (EMT, also known as transdifferentiation) is a process during which cells lose epithelial characteristics and acquire mesenchymal characteristics. Loss of E-cadherin is considered a hallmark event of EMT. Concurrent with that loss, transdifferentiating cells acquire mesenchymal characteristics, including increased expression of N-cadherin. Collectively, the down-regulation of E-cadherin and the upregulation of N-cadherin serves as a marker of EMT (Xu et al., *Cell Res.* 19:156-172, 2009). The EMT has been studied both during development and in the context of cancer progression. In a study of developing human teeth, Heymann reported that, although both E- and N-cadherin were expressed in embryonic dental tissues, their expression patterns were markedly different (Heymann et al., *Am. J. Pathol.* 160(6):2123-2133). E-cadherin was initially expressed in the dental epithelium at the cap stage and was down-regulated when ameloblast differentiation began at the bell stage. N-cadherin showed an inverse gradient compared with E-cadherin and was up-regulated in differentiated epithelial cells (Heymann, supra). According to Heymann, increased expression and apical localization of N-cadherin play an important role in ameloblast transformation and polarization that is a prerequisite for enamel matrix secretion. In a study of cancer progression, Araki et al. employed a model system in which EMT was induced with recombinant TGFβ1 and found that the switch from E- to N-cadherin promoted cancer progression via TGFβ1-induced EMT in extrahepatic cholangiocarcinoma (*Br. J. Cancer* 105:1885-1893, 2011).

In the present methods, differentiated cells (e.g., primary or immortalized oral epithelial keratinocytes) can be induced to undergo dedifferentiation and to express N-cadherin by treatment with a transforming growth factor. As reported below, we observed a reduction in E-cadherin expression and an increase in N-cadherin expression in oral epithelial keratinocytes treated with TGFβ1. We also observed the induction of amelogenin expression upon treatment with serotonin. We have confirmed the induction of amelogenin following treatment with 10 μM serotonin for 10 days, and this treatment protocol can be adjusted (e.g., one can test for and observe amelogenin production following treatment with about 1-100 μM (e.g., about 5-80 μM) for about 2-20 days).

One can test a sample of the cells within a given culture for expression of the markers discussed above or any others at any time during the process of forming an enamel product. For example, a sample of the cultured cells can be fixed (e.g., in alcohol (e.g., 100% methanol)) and subjected to immunohistochemistry with a custom-made or commercially available antibody.

In some embodiments (e.g., when the first cell cultured is a dedifferentiated cell), growth factors can be present from the time the cells are placed in culture. In other embodiments (e.g., when the cells initially placed in culture are differentiated cells), the growth factor(s) can be added at a later stage, such as following dedifferentiation and/or after exposure to a re-differentiation agent (e.g., a serotonin receptor agonist).

Growth factors and other agents that may be added to facilitate cell growth and the enlargement of enamel organoids include the following in any combination: amphiregulin; epigen; EGF; FGF (FGF1, FGF2, FGF3, FGF4, FGF5, FGF6, FGF7, FGF8, FGF9); IGF (IGF1, IGF2); insulin; PDGF; hepatocyte growth factor; WNT; TGFβ; chemokines and cytokines (e.g., an interleukin such as IL-1 or IL-6); Notch ligand; PGE; $PGE_2$; EP1, EP2, EP3, EP4; Noggin; nicotinamide—used in organoids for tumors; A8301 (a potent inhibitor of TGFβ type 1 receptor ALK5 kinase, type I activin/nodal receptor ALK4 and type 1 nodal receptor ALK7); R-Spondin; Flk1; BMPs; ActivinA; Oct4; SOX-9, SOX17; Runx; LEF1; calcium hydroxyapatite; tuftelin; and dentin sialophosphoprotein.

For example, cultures of enamel organoids can include EGF at 0.1-100 ng/ml of culture medium, soluble E-cadherin at 0.1-100 ng/ml of culture medium, fetal bovine serum (10%), and/or calcium at 0.1-10 mM. The growth factors can be added to the growth media initially (i.e., at the time the cells are placed in culture) and can also be present after the cells are transferred from a two-dimensional to a three-dimensional culture system (e.g., a system including the scaffold materials described herein).

Figure 6:
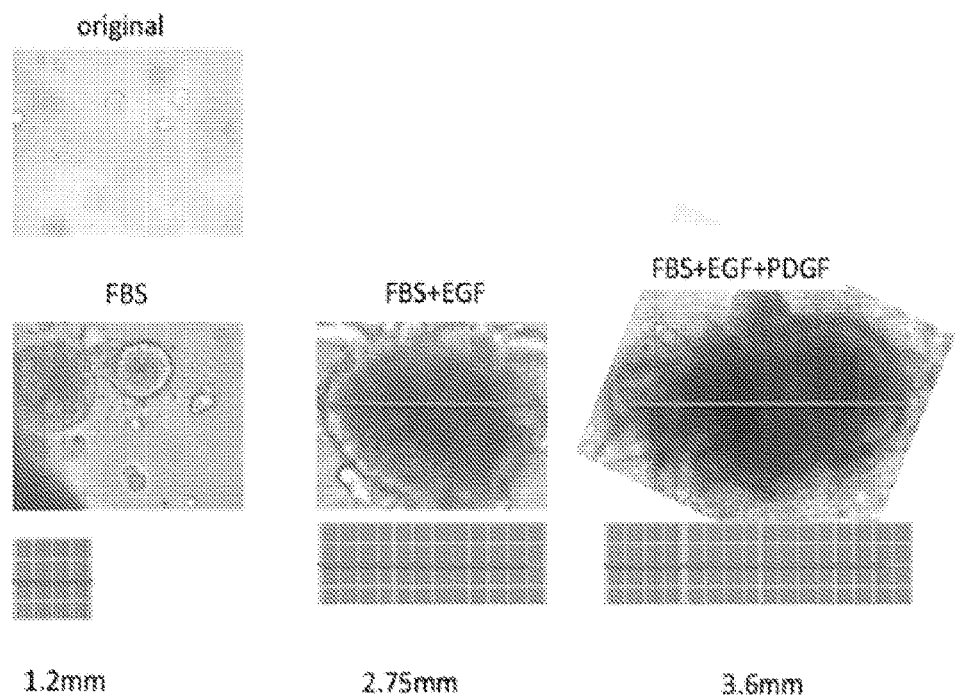
FIG. 6 is a series of photographs of enamel organoids in culture. The photograph labeled "original" depicts enamel organoids prior to incubation with any growth factor(s). The remaining photographs show the effect of culturing the seeded organoids with fetal bovine serum (FBS), FBS and EGF, or FBS, EGF, and PDGF.

The cells and/or enamel organoids that develop therefrom can be seeded at different densities depending on the desired proximity for conglomeration. To generate larger organoids (e.g., having a diameter of more than one mm and up to, e.g., 50 mm) the cells can be seeded more densely such that they contact one another when grown in culture (e.g., in the presence of growth factors, such as those in FBS, EGF, and PDGF, as shown in FIG. 6).

Mineralization: We have also observed the deposition of calcium in the extracellular matrix upon treatment with a mineralizing solution (calcium 2.5 mM, phosphate 1.5 mM). Stock solutions of calcium (at, e.g., 30 mM) and phosphate (at, e.g., 3 mM) can be prepared using reagent grade $CaCl_2.2H_2O$ (Sigma, >99.0% pure) and $KH_2PO_4$ (Sigma, >99.0% pure). The $KH_2PO_4$ solution can be adjusted to pH 7.4 at 25° C. using a small volume of KOH, and solutions can be filtered prior to use. Other solutions that can be used in mineralization include 10% calcium gluconate solution, 1% sodium fluoride solution, and 3% remodent solution.

Removal of organic material: As noted, in any of the present methods, the enamel organoids (e.g., mineralized enamel products) can be treated to reduce or remove some (e.g., substantially all) of the organic material (e.g., cellular material, including proteins, fats, and nucleic acids) therein. For example, the enamel organoids can be treated with (e.g., immersed in) sodium hypochloride and/or a soap/detergent (e.g., Triton-X100). If desired, the treatment can include immersing the enamel organoids in an ultrasonic bath and/or exposing them to heat (e.g., dry heat) to facilitate the destruction and/or removal of the organic material. Organic materials can also be removed by exposure to solutions including appropriate enzymes, such as proteases and nucleases. The enamel products as described herein can therefore be free or substantially free (e.g., more than 90%, 95%, 98% or 99% free) of organic matter.

Additional agents, such as colorants, can be added to any enamel product before or after it is made into or incorporated into a restoration or prostheses. For example, the colorants used to change the color or natural enamel or dental veneers can be incorporated by methods known in the art.

Characteristics of the enamel organoids and the enamel produced thereby: Like naturally occurring enamel organs, the enamel organoids produced by the present methods can have a spheroid appearance; the enamel organoid is a sphere that grows via expansion in three dimensions, and the peripheral borderline cells of the enamel organoids grow similarly. Within the constructs, the peripheral borderline cells lay down extracellular matrix that provides the basis for mineralization and enamel. The constructs can include calcified nodules, and the appearance of these nodules (in size and/or number) can be facilitated by a transforming growth factor (e.g., TGF-β). Growth factors (e.g., TGF-β) can also influence the expression of markers of differentiation, including those discussed below. The organoids in culture typically have a spheroid shape, and they can be harvested and shaped into cubes (e.g., ~1 $cm^3$ cubes). In the methods of the invention, the cubes can then be mounted on a post that can secure the enamel product to a milling machine that will shape the product based on CAD/CAM methodology. In some embodiments, where the enamel product is used to generate a larger surgical restoration (e.g., a restoration for a substantial replacement of bone or augmentation of an existing bony structure), the organoids that develop in culture can be fused into a matrix of essentially any shape utilizing smaller, interlocking pieces. In other words, the organoids, whether shaped (e.g., as blocks) or unshaped, can be assembled if necessary or more convenient, and such assemblies as well as methods of making and using them are within the scope of the present invention.

Markers of differentiation: Amelogenin, ameloblastin, tuftelin, enamelin, MMP-20 (matrix metalloproteinase-20), and EMSP1 (enamel matrix serine proteinase 1), and cytokeratin 14 are suitable markers for ameloblast differentiation in vitro and in vivo.

Like naturally occurring enamel, the enamel products produced by the methods described herein can have a high mineral content, including hydroxyapatite, which is a crystalline calcium phosphate. Hydroxyapatite may constitute at least 50% (e.g., at least 50%, 60%, 70%, 75%, 80%, 85%, 90%, 95%, 96%, 97%, 98%, 99% or more) of the enamel product by weight. Said differently, in various embodiments, the enamel product comprises at least 50% (e.g., at least 50%, 60%, 70%, 75%, 80%, 85%, 90%, 95%, 96%, 97%, 98%, 99% or more) hydroxyapatite by weight. Mineral content and other properties can be determined by further testing, such as X-ray crystallography. The enamel products can also contain at least one type of protein selected from within the two unique classes of proteins, namely proteins of the amelogenin and enamelin classes, which are believed to serve as a framework for mineralization (see, e.g., Catalano-Sherman et al., *Calcif. Tissue Int.* 54(1):76-80, 1994) and/or fragments or naturally occurring small isoforms thereof.

As noted, the enamel products of the invention can be further shaped and manipulated, and we expect blocks that are about 1 $cm^3$ in size will be a convenient size for many applications and readily amenable to CAD/CAM technology. To grow the enamel organoid to an appropriate size for the intended eventual use, the enamel organoids produced in vitro (as described herein), can be exposed to a cocktail for growth including, for example, serum and one or more growth factors including, but not limited to an FGF, EGF, IGF, insulin, and/or soluble cadherins, such as soluble E-cadherin (provided by Dr. Sabine M. Brouxhon; Stony Brook University).

Methods of fashioning restorations: An enamel product generated as described herein can be used in any technique that is suitable for fashioning dental restorations from existing materials. For example, impression molding can be used to manually develop a restoration. Alternatively, the restorations can be made by a system that utilizes scanning technologies, such as laser scanning, photographic imaging (see U.S. Pat. No. 5,851,115, the content of which is hereby incorporated herein), and mechanical sensing (see U.S. Pat.

No. 5,652,709, the content of which is hereby incorporated herein). In one embodiment, the method includes the steps of imaging a body area and a replacement part with a single imaging device which is arranged to take a simultaneous picture of the body area from different angles during one exposure. The pictures are developed and scanned with a reading device which generates digitized data of the imaged body area and the replacement part to be applied in that area. The digitized data is transmitted to computer equipment which automatically reproduces the body area and replacement part on a screen. A computer program calculates spatial relations data of surfaces of the body area and replacement part, and the data is used as control data in making and fitting the replacement part in the body (e.g., a human body).

After scanning, technicians can create the restoration, optionally using a computer-aided design package. CAD/CAM (Computer-Aided Design and Computer-Aided Manufacturing) technology has been used to provide many of the currently available dental restorations, including crowns, veneers, a corresponding scaffold, inlays, onlays, and bridges (e.g., fixed bridges), and it can be similarly used with the present enamel products. The materials historically employed in this process include metals, porcelains, and composites that have remarkably different mechanical properties from those of the natural tooth. For example, these materials can vary greatly with respect to hardness, elasticity, and their temperature coefficients. Such differences can allow for microleakage around the restoration and subsequent dental caries. An advantage of the present invention is that the enamel products produced by the present methods more closely resemble natural enamel and can also be subjected to CAD/CAM milling and dental restorative applications. Consequently, the resulting dental restoration exhibiting properties that are more similar to those of the natural tooth, and the same can be said where the mineralization is tailored such that the hardness of the enamel products more closely approximates that of cartilage or bone.

Accordingly, the invention features methods of fashioning the enamel products described herein (or made by a method described herein) into restorative dental products and skeletal prostheses. The restoration may be a traditional lab-created fixed restoration or may be produced on a CAD/CAM designing and milling system such as that sold under the tradename CEREC by Sirona Dental Systems. Other dental software products that can be used with the present enamel include Delcam™, Renishaw™, and WorkNC Dental™. Utilization of a CAD program is described in U.S. Pat. No. 5,338,198, the content of which is incorporated herein by reference. Generally, conventional dental impressions can be digitized by a computer-controlled laser scanner, and such a digitizing step can be included in the present methods of fashioning an enamel product. Subsequently, the data can be transformed by customized computer graphics software so the derived 3D electronic models (e.g., of the teeth, dental arches, or damaged bone) can be viewed on a computer screen from various perspectives and at various magnifications.

In one embodiment, a rapid prototype of a patient's dentition and dental implant analog can be made using the techniques described in U.S. Pat. No. 8,612,037, the content of which is hereby incorporated by reference herein. Copy milling methods can also be used.

One of ordinary skill in the art of dental restorations will be familiar with products such as crowns, veneers, corresponding scaffolds, inlays, onlays, dentures and bridges. Briefly, a crown is a tooth-shaped "cap" that, when placed over the tooth, improves its shape and size, strength, and appearance. Crowns are generally cemented into place and fully encase the visible portion of the tooth. Patients who require crowns include patients whose teeth are weakened (e.g., by decay, breakage, or severe wearing) and patients seeking a cosmetic improvement. For example, crowns can be placed over misshapen or badly discolored teeth, and they can also be placed over a dental implant.

In other embodiments, the restorative dental products and skeletal prostheses can be made by 3D printing using particles of the enamel products to print the desired restoration. In other words, one can use the enamel crystals produced by the enamel organoids of the invention to form larger structures (i.e., essentially any restorative dental product or skeletal prosthesis) with the assistance of 3D printers, and such methods are within the scope of the present invention. Alternatively, one could use a 3D printer to print an organic matrix (e.g., of extracellular matrix material) that serves as the frame for the restoration. One would then place the frame in culture with cells as described herein (e.g., ameloblast-like cells) that will adhere to the frame. Once the frame is populated, the scaffold and extracellular matrix produced by the cells can be mineralized to the desired extent and the organic matter can be removed, leaving the final enamel restoration ready for implantation.

With regard to the implantation procedure, dental restorations made as described herein can be implanted using known techniques, including techniques allowing for minimal amounts of cement to extend beyond a margin as described in U.S. Pat. No. 8,641,419, the content of which is hereby incorporated by reference in its entirety. Briefly, a barrier is positioned in contact with the tooth being restored and an adjacent tooth to cover a section of the tooth being restored and to create separation of the tooth being restored and the adjacent tooth. Cement is applied to the first mating surface of the fixed restoration and/or to the second mating surface of the tooth, and the first mating surface of the fixed restoration and the second mating surface of the tooth are positioned adjacent each other to seat the fixed restoration on the tooth. The barrier covers a section of the tooth being restored to prevent cement from bonding to the section of the tooth. This eliminates the need to remove hardened cement from this section of the tooth.

EXAMPLES

In the studies described below, the ameloblast-like cells originated from oral epithelial keratinocytes. We employed the cell line IMOK, an immortalized oral keratinocyte cell line of mouse origin, which was a gift from Dr. Garrett-Sinha (SUNY-Buffalo; Parikh et al., *Arc. Oral Biol.* 53:1091-1100, 2008).

To thaw frozen IMOK cells, we removed a cryovial containing $10^6$ frozen cells from liquid nitrogen storage, immediately placed it into a 37° C. water bath, and gently swirled the vial. When the cells were thawed, we transferred the vial into a laminar flow hood, and added 10 ml of pre-warmed serum free CnT-02 growth medium (CELLNTEC; FPS 1:1000 added to the medium). We centrifuged the cell suspension (~1000 rpm for 4 minutes) then checked the vial visually for the presence of a complete pellet. The supernatant was aseptically decanted without disturbing the cell pellet, which we gently resuspended in 7 ml of CnT-02 medium. We transferred the resuspended cells into a T25 flask and incubated it at 37° C. with a humidified atmosphere of 5% $CO_2$ The medium was changed every other day, and when the cells became 90% confluent, we split them 1:5 and plated them in a 12-well plate as follows. After discarding the culture medium from the flask, we washed the cells with PBS then added 2 mL of a pre-warmed dissociation reagent (TrypLE; GIBCO), gently shaking the flask to completely cover the cell layer. We transferred the flask to the incubator (37° C., 5% $CO_2$) for 20 minutes, checking under a microscope every 5 minutes for dissociation of the cells. When ≥90% of the cells detached, we added 8 ml of pre-warmed CnT-02 growth medium (CELLNTEC), dispersing it with a pipette over the cell layer surface several times. The cell suspension was transferred to a 50 ml conical tubed and centrifuged (1000 rpm for 4 minutes). We resuspended the cell pellet in 5 ml of pre-warmed serum free CnT-02 growth medium (CELLNTEC) and split the cells in 1:5 ratios. We diluted the cell suspension plate and pipetted the appropriate volume into new 12-well plates, returning the cells to the incubator (37° C., 5% $CO_2$).

When the split cells reached 30-40% confluence, we began treating them with 5 ng/ml TGFβ1 (rhTGFβ1; R&D system). We added the vehicle (4 mM HCl+1 mg/mL BSA) to the control side and TGFβ1 (5 ng/mL) to the experimental side and mixed gently. We changed the medium every other day for 10 days. To fix the cells, we aspirated the medium, washed the cells with PBS then fixed them with 100% methanol for 20 minutes. Following fixation, we washed the fixed cells with PBS (×3) and stored them at 4° C.

Immunocytochemistry General Protocol: (1) wash sample slide in 0.15 M PBS (pH 7.2; 4×5 minutes); (2) incubate in 4% Normal Goat Serum (NGS) for 20 minutes (2 ml of 0.15 M PBS+80 μL NGS); (3) incubate with the primary antibody solution (details below; 90 minutes); (4) wash with 0.5 M PBS (3 times×10 minutes); (5) block with 4% NGS in 0.15 M PBS (20 minutes); (6) incubate with the secondary antibody (Biotin-SP-conjugated goat anti-rabbit IgG; 60 minutes); (7) wash with 0.15 M PBS (3 times×10 minutes); (8) prepare and incubate in ABC solution (details below; 60 minutes (5 mL of 0.15 M PBS+ABC solution 600 μL); (9) wash with 0.1 M AI buffer (175 mM sodium acetate and 10 mM imidazole, pH 7.2) for 3 times×10 minutes [14.35 g sodium acetate, 0.68 g imidazole in 1000 mL $H_2O$]; (10) carry out DAB reaction for 5-20 minutes, checking often; and (11) wash for 15 minutes in 0.05 M PBS with 0.04% TritonX-100 to stop the reaction.

The primary antibody solution contains 0.15 M PBS with 0.5% Triton X-100; 4% NGS in [0.15 M PBS with 0.5% TritonX-100; and the primary antibody at a 1:500 dilution (2 mL PBS+0.04% Tx 100+80 μL NGS+4 μL primary antibody). The secondary antibody solution contains 0.15 M PBS with 0.5% Triton X-100 and the secondary antibody at a 1:2500 dilution (Goat anti Rabbit IgG) [2 ml PBS+0.04% Tx 100+0.8 uL GαR]. To prepare the ABC (Avidin Biotin Complex) solution, add 1 drop of A, 1 drop of B, to 500 μL of 0.15 M PBS in an Eppendrof tube. Leave it at room temperature on a shaking platform for 30 minutes. The DAB solution contains 50 mL of 125 mM sodium acetate buffer, pH 9.3, to which we added 10 mg DAB (stir until dissolved) and 16.5 μL of 30% $H_2O_2$.

Immunocytochemistry for N-cadherin, E-cadherin, Collagen-1, Amelogenin, and OCT4: To stain for N-cadherin, we used a rabbit polyclonal N-cadherin antibody (diluted 1:1000; ab12221) as the primary antibody and a goat anti-rabbit antibody (1:2500) as the secondary antibody. To stain for E-cadherin, we used a rabbit polyclonal E-cadherin antibody (1:500; H-108 [SC-7870]) as the primary antibody and a goat anti-rabbit antibody (1:2500) as the secondary antibody. To stain for collagen-1, we used a goat polyclonal collagen antibody (1:500 [Col 1A1 (D-13)] [SC-25974]) and a goat anti-donkey secondary antibody (1:2500). To stain for amelogenin, we used a rabbit polyclonal amelogenin antibody (1:500; Amelx; ab59705) as the primary antibody and a goat anti-rabbit antibody (1:2500) as the secondary antibody. To stain for OCT4, we used a rabbit polyclonal Oct4 antibody (1:1000) as the primary antibody and a goat anti-rabbit antibody (1:2500) as the secondary antibody.

Figure 1B:
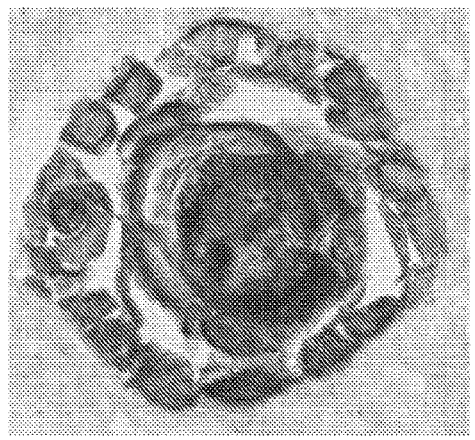
Figure 4:
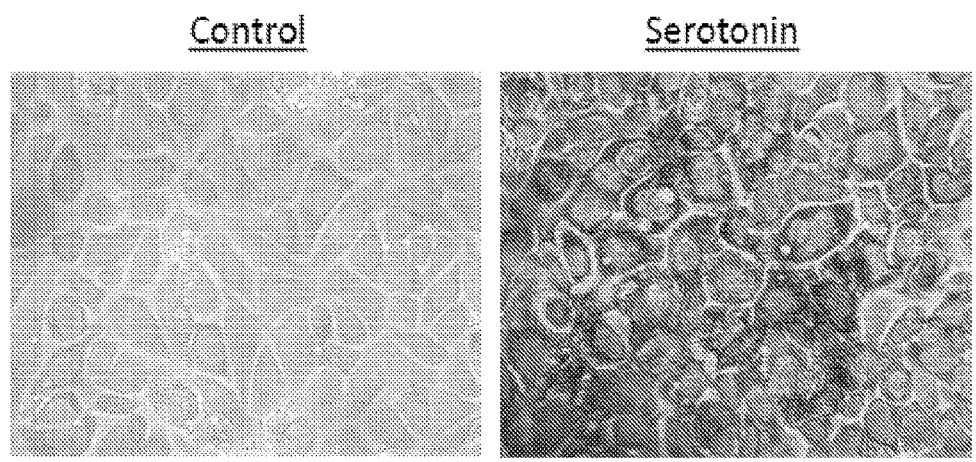
FIG. 4 is a pair of photomicrographs demonstrating the induction of amelogenin expression in the cell line IMOK upon treatment with serotonin.

As shown in FIG. 1(b), the expression of amelogenin in the cells and extracellular matrix of the enamel organoids treated with the transdifferentiation factors TGFβ1 and serotonin provides evidence that the cells adopted the characteristics of ameloblasts. More specifically, as shown in FIGS. 3(a)-3(f), oral epithelial keratinocytes, under the influence of TGFβ1, acquire the expression of Oct4 (b) and lose the expression of collagen1 (d). The cells do not express amelogenin either before (e) or after (f) TGFβ1 treatment. However, when the cells are further treated with serotonin, they express amelogenin (FIG. 4).

Serotonin, serotonin receptors, and the developing tooth: Serotonin receptors have been identified in the mouse enamel organ in vivo (Riksen et al., Eur. J. Oral Sci. 118:566-573, 2010). Adding serotonin to organotypic mouse cultures containing developing tooth buds induced downstream pathway activation and accelerated tooth development, which was reversed with antagonists (Moiseiwitsch and Lauder, Arc. Oral Biol. 41:161-166, 1996; Moiseiwitsch et al., Arc. Oral Biol. 43:789-800, 1998). Targeted deletion of the serotonin 5TH2B receptor in mice resulted in structural alterations of mouse dental tissues (Dimitrova-Nakov et al., Calcif. Tissue Int., 94(3): 293-300, 2014). Collectively, these data show that serotonin signaling plays a role in dental development.

Treatments with TGFβ1 and serotonin: We treated the IMOK cells that were thawed and cultured as described above with TGFβ1 (5 ng/ml) for 10 days and then with serotonin (100 μM) for another 10 days. In the initial study, we used two 12-well plates with cells at 30-40% confluence. We treated the experimental side with TGFβ1 (5 ng/ml) for 10 days, and we added the same amount of vehicle to the control side (4 mM HCL+1 mg/ml ABS). We changed the medium every other day. After a 10-day treatment with TGFβ1, we treated two plates as follows. On IMOK plate #1, we continued the TGFβ1 treatment (5 ng/ml) and added serotonin (100 μM) to the experimental side. On IMOK plate #2, we added 100 μM serotonin to the experimental side and vehicle to the control side. We changed the medium every other day for 8 days. To fix the cells, we exposed them to 100% methanol for 20 minutes, washed them with PBS (3×) and stored them at 4° C.

We also tested the effect of different serotonin concentrations on IMOK cells treated for 10 days with TGFβ1. The cells were split 1:8, and we changed the CnT-02 serum free medium every other day. When the cells reached 40% confluence, they were treated with TGFβ1 (5 ng/ml) for 10 days before serotonin was added at concentrations of 1 nM, 10 nM, 100 nM, 1 μM, 10 μM or 100 μM to selected wells. We continued TGFβ1 (5 ng/ml) treatment in other wells of the plate as a control. We changed the medium every other day for another 10 days the fixed the cells with 100% methanol and stored them at 4° C.

We established 2- and 3-dimensional cultures of the IMOK cells to study the effect of a mineralization solution on cells treated with TGFβ1 and serotonin. After we thawed the cells, they were placed in a T25 flask with serum free medium CnT-02 (changed every other day). When the cells reached 40% confluence, we treated them with TGFβ1 (5 ng/ml) for 10 days then plated and treated them with serotonin 10 μM for 10 days (continuing to change the medium every other day). 2-D cultures were fixed with 100% methanol and 3-D cultures were fixed with 10% formalin. We added hydroxyapatite (HA) to group which haven't been fixed and changed the media every other day.

To produce 3-D cultures, we used BD Matrigel™ Basement Membrane Matrix (cat #356234) and pre-cooled the pipettes, tips, and tissue culture ware at 4° C. overnight. In a process we refer to as the "thick gel method," we thawed the gel overnight at 4° C. on ice then diluted it with serum-free media (CnT-02) 1:1 (gel:medium) and mixed well. We kept the culture plates on ice and added gel to cell culture wells (plating density 1:5 split) at 150-200 µl/cm$^2$ of growth surface. After incubating the cells at 37° C. for 30 minutes, we added 1 ml of medium to each well.

We exposed cells that had been treated with TGFβ1 and serotonin as described above to a mineralizing solution described by Wiedemann-Bidlack et al. (*J. Struct. Biol.* 173(2):250-260, 2011) Stock solutions of calcium (30 mM) and phosphate (30 mM) were prepared using $CaCl_2.2H_2O$ (Sigma) and $KH_2PO_4$ (Sigma). The $KH_2PO_4$ solution was adjusted to pH 7.4 at room temperature, and both solutions were filtered through 0.22 µm filters prior to use. Final concentrations of 2.5 mM calcium and 1.5 mM phosphate were added to the plate (thus generating a mineralization solution). We cultured the cells with mineralizing solution for 10 days and changed the media every other day.

To prepare frozen sections, we fixed the cultures with 10% formalin overnight then washed them with PBS for one hour. We collected the gel in filter paper, embedded it in 30% sucrose for one hour then in OCT at 29° C. The frozen tissues were sectioned on a cryostat (−29° C.) using standard techniques to about 5 µm, and sections were placed on a Fisher Superfrost™ slide and dried overnight at room temperature. We fixed the slides by immersing them in cold acetone (−20° C.) for two minutes. After they air-dried, we proceeded to stain them. Other suitable fixatives include alcohol, formal alcohol, formalin, and others.

Figure 1C:
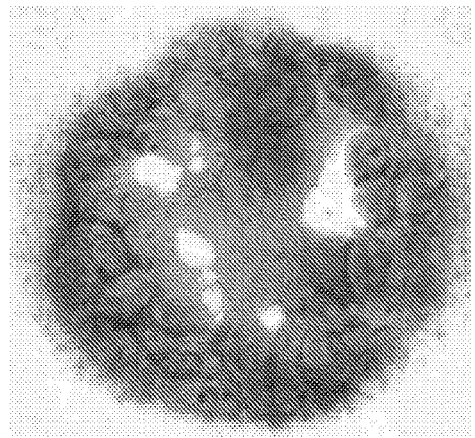
Figures 2A, 2B, 2C, 2D:
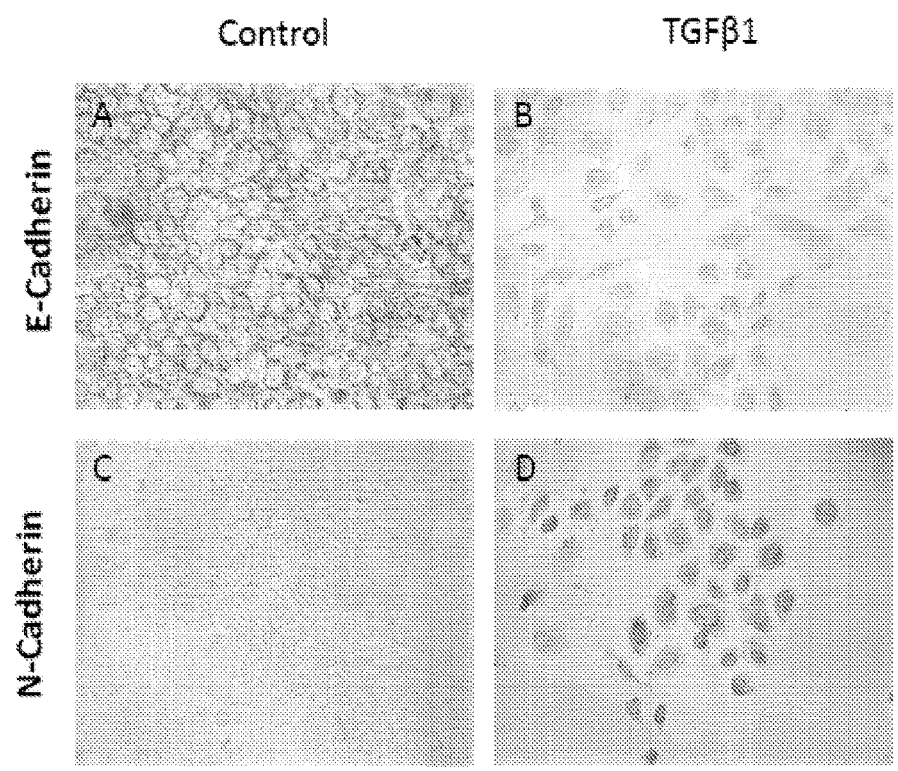
FIGS. 2(a)-2(d) are photomicrographs demonstrating that E-cadherin expression is lost and N-cadherin expression is gained in oral epithelial keratinocytes of the cell line IMOK treated in culture with TGFβ1.
Figures 3A, 3B, 3C, 3D, 3E, 3F:
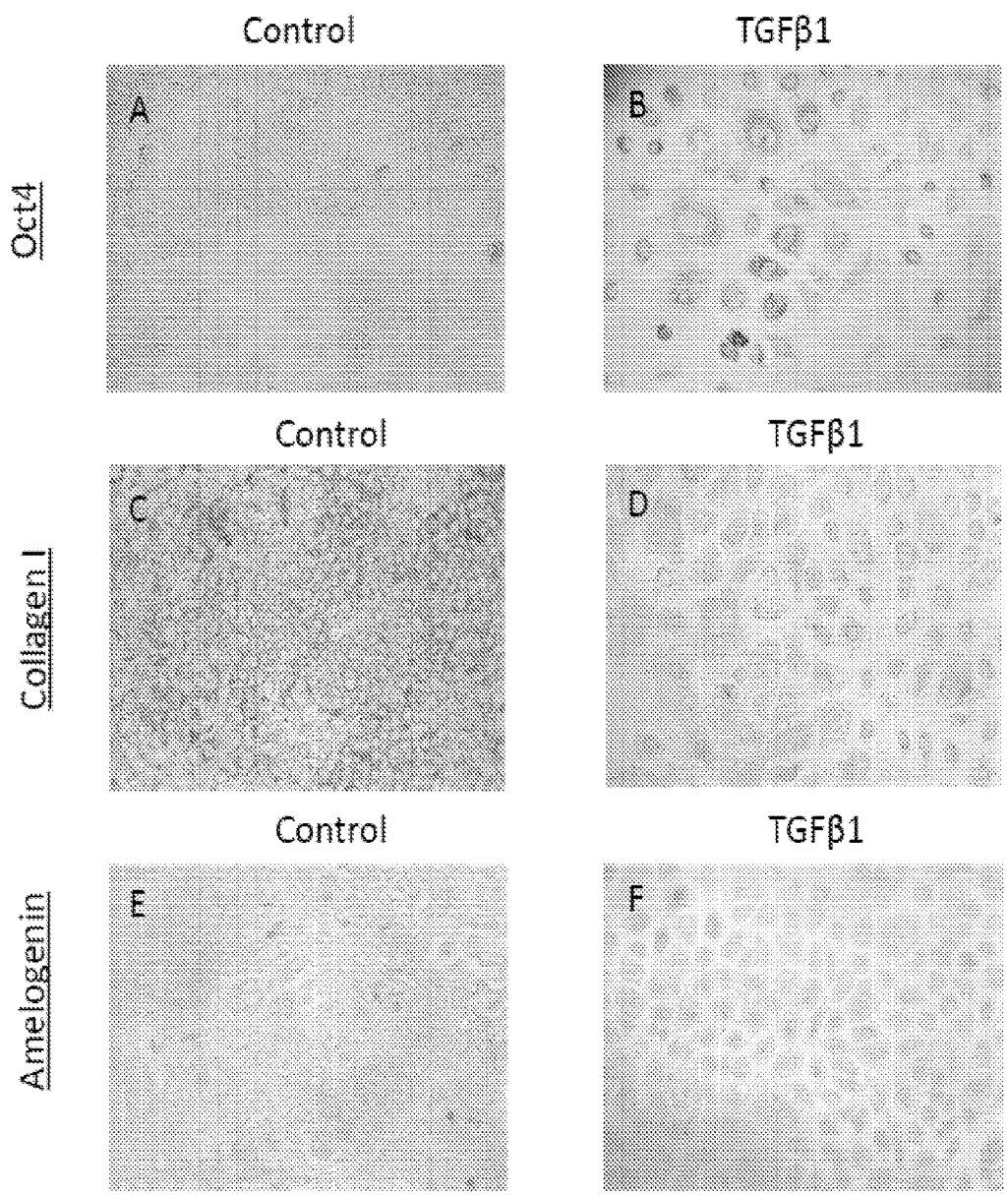
FIGS. 3(a)-3(f) are a series of photomicrographs of oral epithelial keratinocytes of the cell line IMOK stained with antibodies against Oct4, collagen1, and amelogenin before and after treatment with TGFβ1.

H&E (haematoxylin and eosin) staining was carried out by standard methods. Briefly, we: (1) stained the air-dried slides with filtered 0.1% hematoxylin for 10 minutes in a 50 ml conical tube; (2) rinsed them in cool running dd$H_2O$ for 5 minutes; (3) dipped them in 0.5% eosin (1.5 g dissolved in 300 ml of 95% EtOH; 12×)) followed by distilled $H_2O$ until the eosin stops streaking, followed by 50% EtOH (10×) and 70% EtOH (10×); (4) equilibrated the slides in 95% EtOH for 30 seconds then 100% EtOH for one minute; (5) dipped them in xylene several times, wiping away the excess with a tissue; and (6) mounted and coverslipped the slides with Cytoseal XYL™. As shown in FIG. 1(*a*), the enamel organoids are spheroidal clusters including a peripheral borderline cell layer characterized by a palisade arrangement. As shown, the cells are polarized columnar cells, and some are cuboidal. The cells have medium volume of cytoplasm and a single cuboidal or oval nucleus.

We stained formalin-fixed cells from 2D cultures with alizarin red. Our working solution could be stored in the dark for up to three months and included 1 g Alizarin Res S (Sigma, Cat. #A5533)+100 ml distilled water. We adjusted the pH to 4.1-4.3 using 0.1% ammonium hydroxide then poured the solution through a sterile filter. After washing the cells with tap water, we stained them with the alizarin red working solution for five minutes then washed them again with tap water.

We also stained frozen sections of 3D cell cultures that had been exposed to hydroxyapatite (HA) or to HA and serotonin with alizarin red. We rinsed the slides quickly with distilled water before applying an alizarin red solution (2%) for 30 seconds to 3 minutes, checking microscopically for the development of orange-red staining. After shaking off the dye solution, we dipped the slides in acetone (20 times) and acetone-xylene (20 times), cleared them with xylene, and mounted them in Permount™. As shown in FIG. 1(*c*), the enamel organoids stained positively for alizarin red, identifying calcium and indicating that the cells induce mineralization (as do ameloblasts).

As shown in FIGS. 2*a*-2*d*, oral epithelial keratinocytes normally express E-cadherin in culture (a). TGFβ1 treatment induces the loss of E-cadherin expression (b). In contrast, N-cadherin is not normally expressed (c) but is induced by TGFβ1 (d). Thus, keratinocytes derived from the oral epithelium can undergo the same E-cadherin-to-N-cadherin switch as the cells in vivo that become ameloblasts. Histologically, the cells are round and attached to each other under confluent control conditions, whereas the cells enlarge in size, separate and spread out after TGFβ1 treatment.

Figure 5:
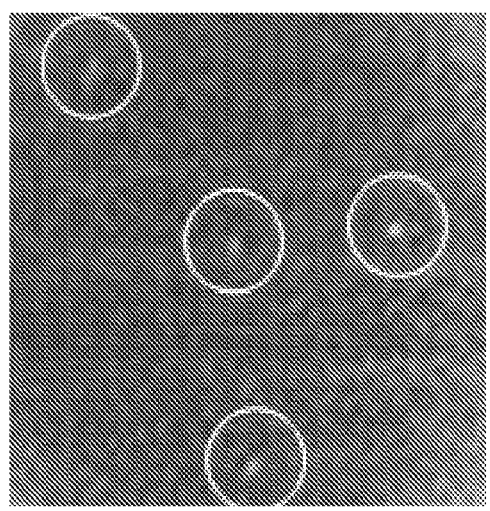
FIG. 5 is a radiograph showing enamel products, which appear opaque and are circled.

Specimens of enamel products produced as described herein appear opaque in radiographs, as shown in FIG. 5.

As noted above, scaffolds can be used to facilitate the production of three-dimensional enamel products. For example, we seeded 3×10$^6$ ameloblast-like cells, believed to be prepared from the IMOK cell line as described above, per scaffold in 48-well culture dishes and allowed the cells to attach to the scaffolds in DMEM containing 10% FCS. The cultures were incubated at 37 with 5% $CO_2$ for 24 hours. The medium was then replaced with cold (4° C.) DMEM to remove the unattached cells and cool down the scaffold. The scaffold-bound cells were then transferred to a new cell culture dish containing cold (4° C.) liquid Matrigel™. We shook the dish gently to facilitate the scaffold's exposure to the Matrigel™ then incubated the dish at 37° C. for 30 minutes. After that time, we added 1 ml of medium to each well, cultured the cells for 10 days, and then cultured them for an additional 10 days in the presence of mineralizing media.

What is claimed is:

1. A method of generating an enamel product in vitro, the method comprising:
    (a) providing an oral epithelial keratinocyte in cell culture;
    (b) exposing the oral epithelial keratinocyte to a transforming growth factor β (TGFβ), thereby producing a dedifferentiated cell;
    (c) exposing the dedifferentiated cell to a serotonin receptor agonist, thereby producing an ameloblast-like cell that produces an extracellular matrix comprising amelogenin; and
    (d) exposing the extracellular matrix to a composition that induces mineralization, thereby producing an enamel product.

2. The method of claim 1, wherein the transforming growth factor β is TGFβ1.

3. The method of claim 1, wherein the dedifferentiated cell expresses N-cadherin and octamer-binding transcription factor 4 (Oct-4) but does not express E-cadherin.

4. The method of claim 1, wherein the serotonin receptor agonist is serotonin, an azapirone, a triptan, LY-334,370, lasmiditan, lysergic acid diethylamide, mescaline, 2,5-dimethoxy-4-bromophenethylamine, lorcaserin, cisapride, tegaserod, prucalopride, AS-19, or a salt, hydrate, or analog thereof.

5. The method of claim 1, wherein the composition that induces mineralization comprises calcium and phosphate and/or the cell culture comprises an epidermal growth factor, an insulin-like growth factor, or a fibroblast growth factor.

6. The method of claim 1, wherein the cell culture: (a) comprises laminin, collagen IV, a heparan sulfate proteoglycan, or entactin/nidogen; (b) comprises a solubilized basement membrane preparation extracted from the Engelbreth-Holm-Swarm (EHS) mouse sarcoma; and/or (c) is configured to permit the ameloblast-like cell to proliferate into a 3-dimensional cluster of cells.

7. The method of claim 1, further comprising a step of exposing the ameloblast-like cell to a composition comprising a growth factor.

8. The method of claim 7, wherein the composition comprises a fibroblast growth factor, a transforming growth factor, or an epithelial growth factor.

\* \* \* \* \*